(12) United States Patent
Lin

(10) Patent No.: US 8,608,694 B2
(45) Date of Patent: Dec. 17, 2013

(54) SELF-LOCKING SELF-DESTROYING SAFETY SYRINGE

(75) Inventor: Zuoqian Lin, Zhejiang (CN)

(73) Assignee: Sol-Millennium Medical Products Co., Ltd, Shanghai (CN)

( * ) Notice: Subject to any disclaimer, the term of this patent is extended or adjusted under 35 U.S.C. 154(b) by 0 days.

(21) Appl. No.: 12/993,936

(22) PCT Filed: Jul. 14, 2008

(86) PCT No.: PCT/CN2008/001309
§ 371 (c)(1),
(2), (4) Date: Nov. 22, 2010

(87) PCT Pub. No.: WO2009/140801
PCT Pub. Date: Nov. 26, 2009

(65) Prior Publication Data
US 2011/0071470 A1    Mar. 24, 2011

(30) Foreign Application Priority Data
May 22, 2008  (CN) .......................... 2008 2 0087169

(51) Int. Cl.
*A61M 5/00*      (2006.01)
(52) U.S. Cl.
USPC ........................................ 604/110
(58) Field of Classification Search
USPC ............. 604/110, 195, 197, 93.01, 220, 218, 604/199, 187, 228, 196, 198, 158
See application file for complete search history.

(56) References Cited

U.S. PATENT DOCUMENTS

| 5,222,942 A | * | 6/1993 | Bader | ............................ 604/110 |
| 2008/0097307 A1 | * | 4/2008 | Walton et al. | .................. 604/110 |

FOREIGN PATENT DOCUMENTS

| CN | 1803212 A | 7/2006 |
| CN | 2820208 Y | 9/2006 |

\* cited by examiner

*Primary Examiner* — Nicholas Lucchesi
*Assistant Examiner* — Brooke Matney
(74) *Attorney, Agent, or Firm* — Ming Chow; Sinorica, LLC

(57) ABSTRACT

The present invention relates to a new self-locking self-destroying safety syringe, which comprises a hollow barrel, a push rod sliding within the barrel, a rubber plug in front of the push rod, and a needle seat in front of the barrel. The push rod is provided with a round platform, which is provided with an elastic ratchet that slantingly extends toward the inner wall of the barrel. The barrel is provided at the end with an increasing-diameter portion. At the transient position between the normal-diameter portion and the increasing-diameter portion of the barrel is located a slanting step, below which is a groove where the elastic ratchet can be catched when the push rod is drawn backward. The increasing-diameter portion of the barrel is provided inside with a circlip that can press against the bottom of the round platform. For a syringe with the above-mentioned structure, the push rod can be locked after injection in the following way: The push rod is provided with the elastic ratchet that extends to the inner wall of the barrel; the elastic ratchet gets stuck into the groove when the push rod is drawn backward; the slanting step above the elastic ratchet prevents the push rod from moving forward, while the circlip below the elastic ratchet presses against the bottom of the round platform of the push rod so as to prevent the push rod from moving backward; and under the action of the groove, the elastic ratchet cannot move radially either.

9 Claims, 7 Drawing Sheets

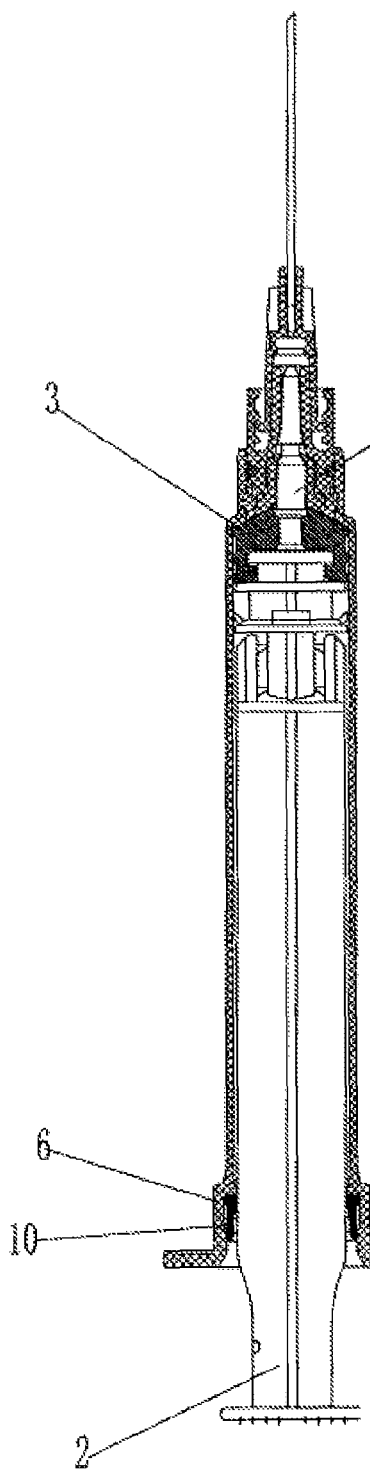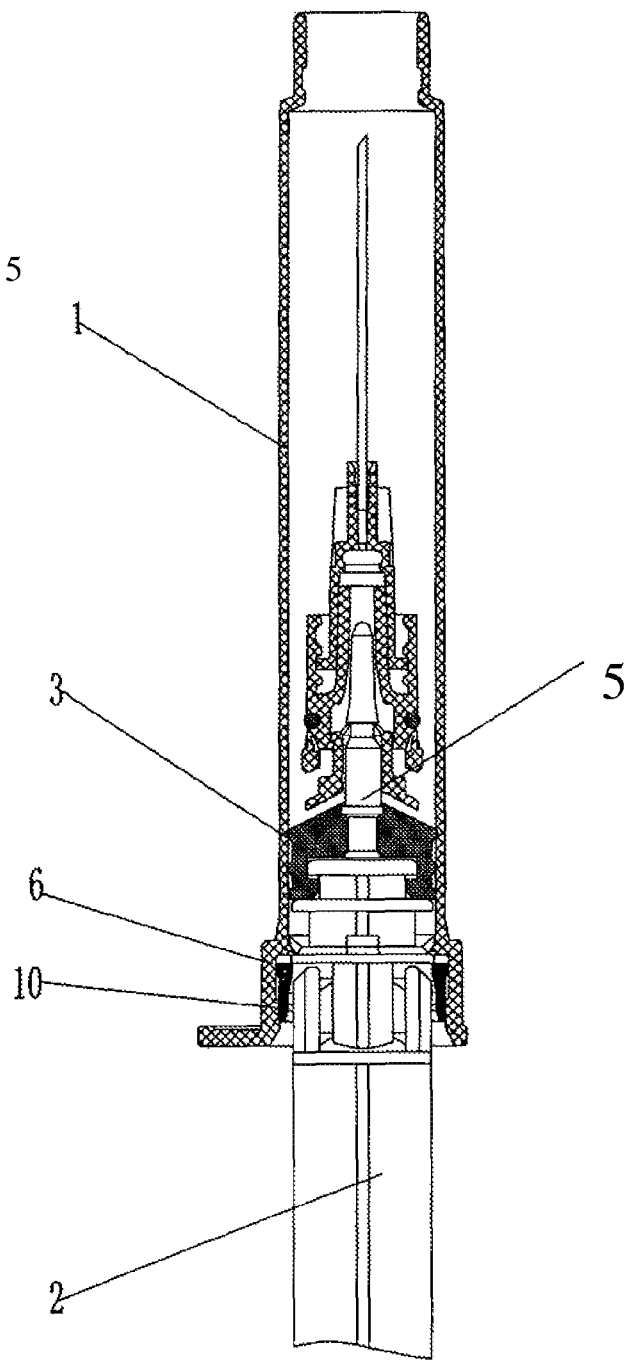
Fig 5
Fig 6

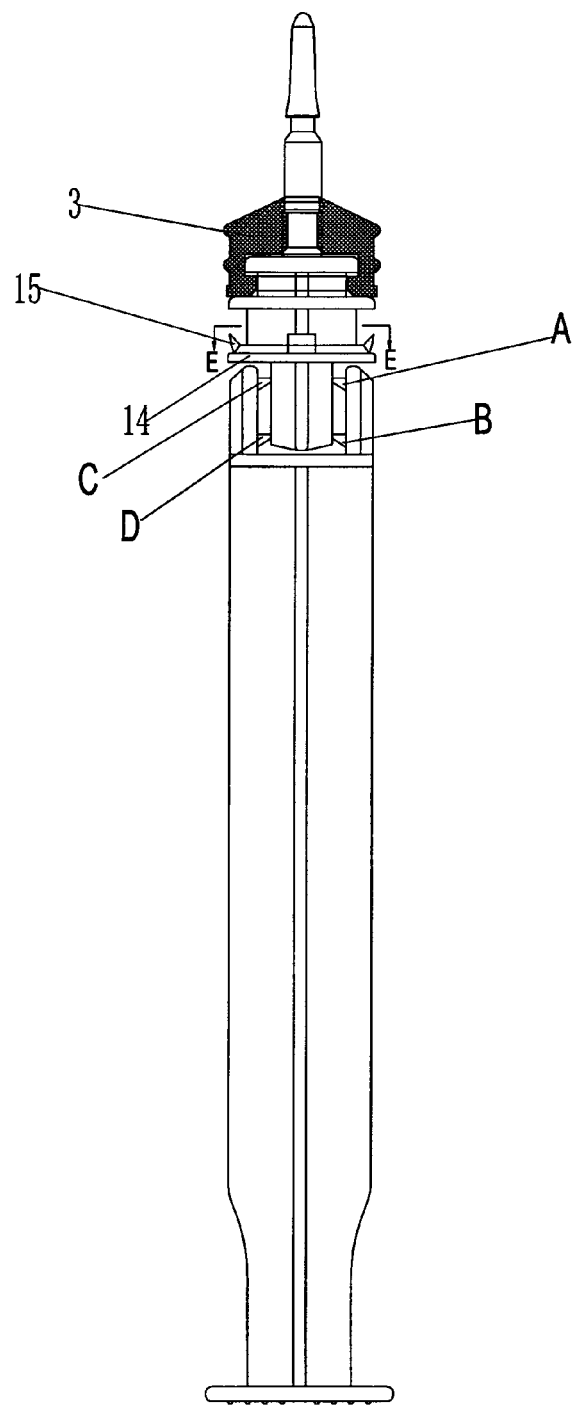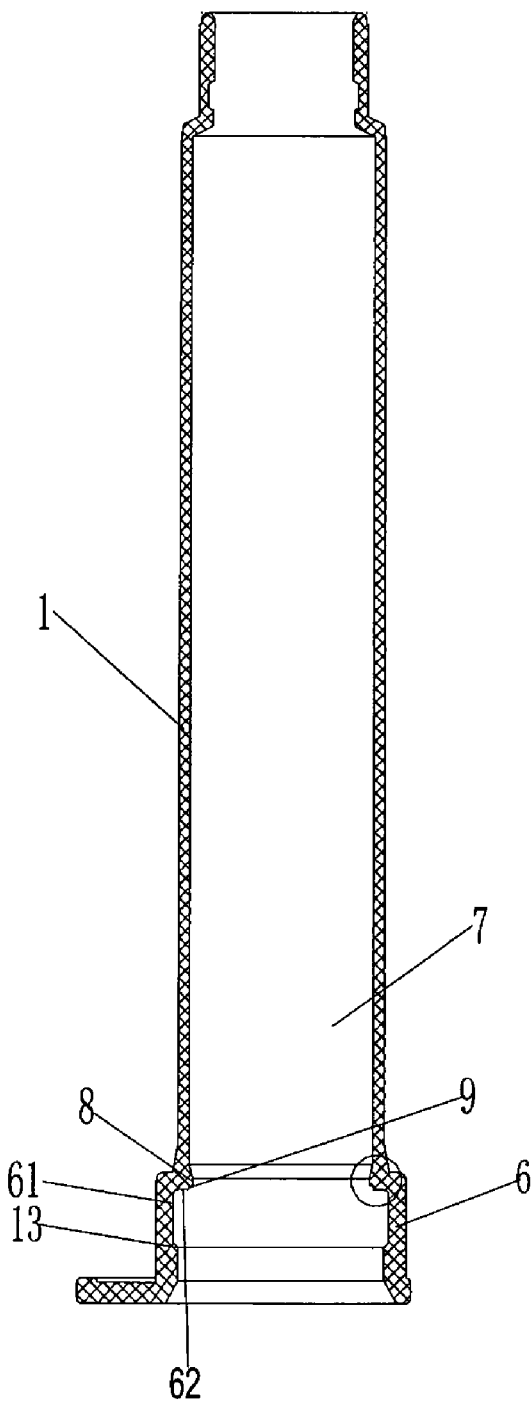
Fig 10
Fig 11

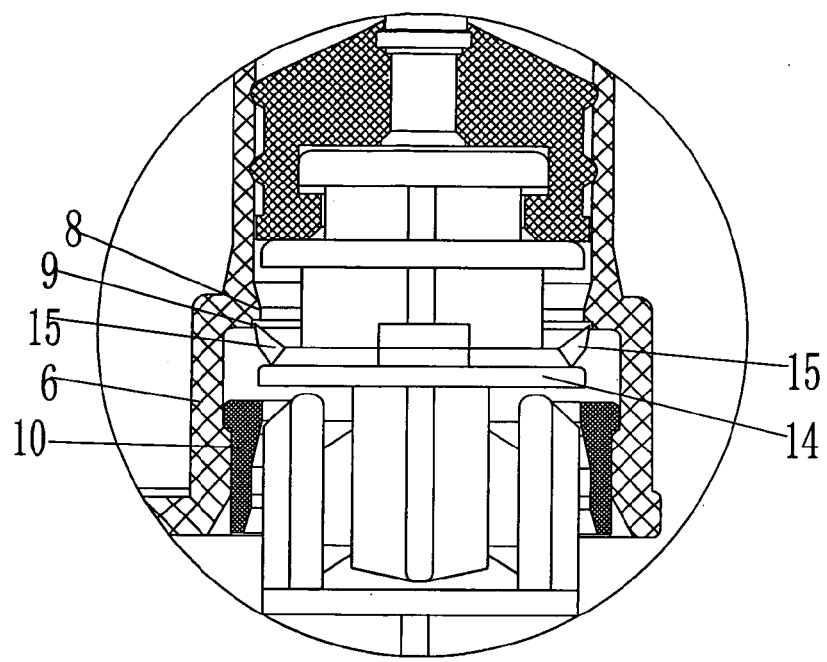
Fig 13
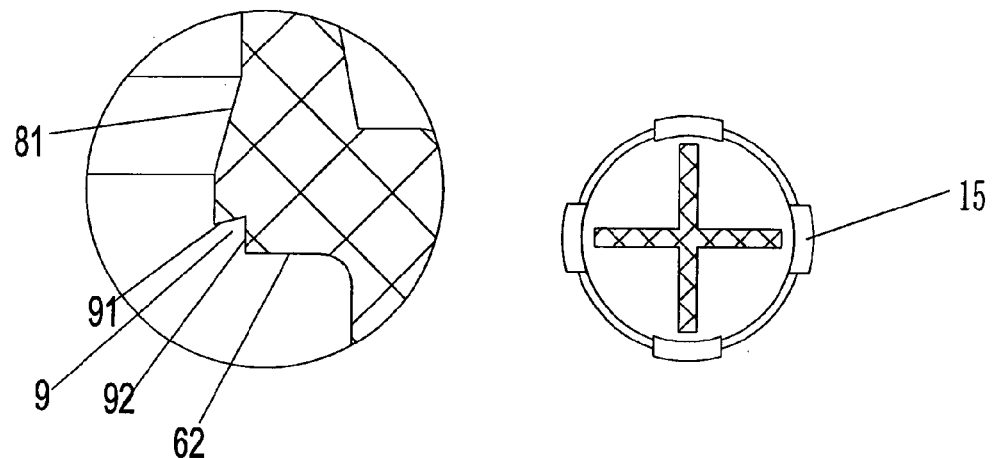
Fig 14                    Fig 15

SELF-LOCKING SELF-DESTROYING SAFETY SYRINGE

FIELD OF THE INVENTION

The present invention relates to a medical apparatus, and particularly to a disposable self-destroying syringe.

BACKGROUND OF THE INVENTION

A syringe is an indispensable apparatus to medical treatment. All current syringes are designed as being disposal so as to prevent cross infection. However, such disposal syringes can be reused if they are not destroyed artificially. In order to prevent the current disposal syringes from being reused, which may result in cross infection and disease spread, many types of syringes have been invented. For example, in a syringe where the needle retracts into the barrel when the push rod is drawn back, the needle may come out again when a force is applied, which may still result in cross infection. In another needle-retractable safety syringe disclosed in the patent No. 200410017938.0, the needle will retract into the barrel when the push rod is drawn back, with the needle tip tilting aside and difficult to be drawn out. However, it is easy for the sharp needle tip to pierce through the barrel wall, which is soft and generally made of common polypropylene (PP). Therefore, this syringe may still result in cross infection. The following three methods may be adopted for the sake of safety: 1. Increasing the thickness of the barrel wall; 2. adding a stiffening agent into the polypropylene raw material; and 3. choosing a barrel with low rigidity. However, the cost will thus be increased, and the sharpness of the needle tip lowered, which may bring much suffering to the patients. The push rod can also be provided with a defective portion. The syringe can be destroyed after injection by breakage of the push rod. However, such a syringe can still be reused so long as the broken push rod is replaced with a new one. Therefore, the complete safety cannot be guaranteed.

Contents of the Invention

A purpose of the present invention is to provide a self-destroying syringe, whose push rod can be locked after injection so that it cannot be reused or replaced.

In order to achieve the above purpose, a technical solution of the present invention is as below:

A new self-locking self-destroying safety syringe is provided, comprising a hollow barrel, a push rod sliding within the barrel, a rubber plug in front of the push rod, and a needle seat in front of the barrel. It has the following features: The push rod is provided with a round platform, which is provided with an elastic ratchet that slantingly extends toward the inner wall of the barrel; the barrel is provided at the end with an increasing-diameter portion; at the transient position between the normal-diameter portion and the increasing-diameter portion of the barrel is located a slanting step, below which is a groove where the elastic ratchet can be catched when the push rod is drawn backward; and the increasing-diameter portion is provided inside with a circlip that can press against the bottom of the round platform.

The circlip, dynamically fitted with the inner wall of the increasing-diameter portion at the end of the barrel, can move forward and backward axially without moving out of the barrel, with the moving distance longer than the distance from the tip of the elastic ratchet on the push rod to the bottom of the round platform; the internal diameter of the upper end of the circlip is slightly smaller than that of the barrel at the slanting step; the circlip is provided at the inner circle with a slope; when the push rod is installed, the elastic ratchet can move forward and furl inward along the slope, and the round platform can stretch the inner bore of the circlip larger and get into it.

The increasing-diameter portion at the end of the barrel is provided on the inner wall with a circle of big groove that is dynamically fitted with the circlip; the big groove can butt at its upper end against the top end of the circlip, and is provided at the lower end with a flanged step; the circlip is provided at the upper outer circle with a flange; and the flanged step butts against the bottom end plane of the outer circle flange.

The external diameter of the round platform on the push rod is smaller than or equal to the minimal internal diameter of the barrel at the slanting step, but bigger than the minimal internal diameter of the circlip.

There are at least two elastic ratchets that are symmetrically positioned; the distance between the symmetrical ratchet tips is smaller than the internal diameter of the normal-diameter portion of the barrel, but bigger than the minimal internal diameter of the barrel at the slanting step.

The tip of the elastic ratchet extends slantingly up to the front end of the barrel.

There are four elastic ratchets that are symmetrically positioned.

The groove is a circle of clamping groove, whose upper end plane is a slope or a plane that extends outward along the direction of the tip of the elastic ratchet; and the diameter of the groove at the side wall is bigger than the distance between the two symmetrically-positioned ratchet tips.

For a syringe with the above-mentioned structure, the push rod can be locked after injection in the following way: The barrel is provided at the end with the increasing-diameter portion; the self-locking mechanism can be located at the rear end of the barrel; the push rod is provided with the elastic ratchet that extends to the inner wall of the barrel; the elastic ratchet gets stuck into the groove when the push rod is drawn backward; the slanting step above the elastic ratchet prevents the push rod from moving forward, while the circlip below the elastic ratchet presses against the bottom of the round platform of the push rod so as to prevent the push rod from moving backward; and under the action of the groove, the elastic ratchet cannot move radially either.

BRIEF DESCRIPTION OF THE DRAWINGS

FIG. 5 is a sectional view of the syringe after injection.

FIG. 6 is a sectional view of the syringe in its first step of the self-destroying process.

FIG. 10 is a sectional view of the push rod.

FIG. 11 is a sectional view of the barrel.

FIG. 13 is a partial enlarged view of FIG. 7.

FIG. 14 is a partial enlarged view of FIG. 11.

FIG. 15 is a sectional view of FIG. 10 along the line E-E.

DETAILED DESCRIPTION OF THE EMBODIMENTS

Figure 1:
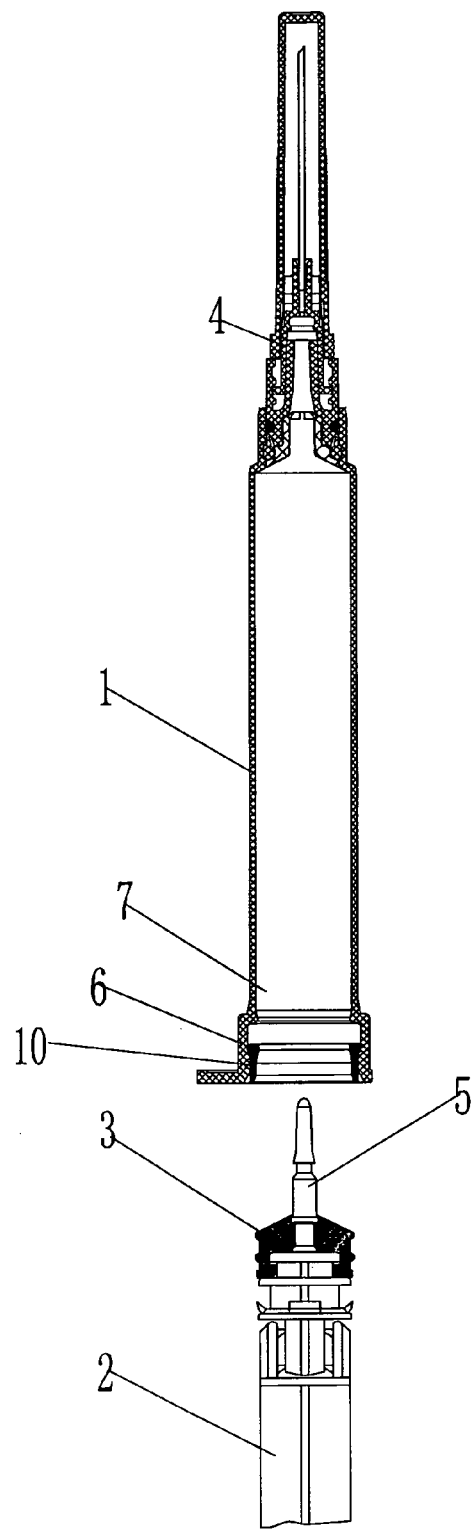
FIG. 1 is a sectional view of the syringe before the push rod is installed.
Figure 2:
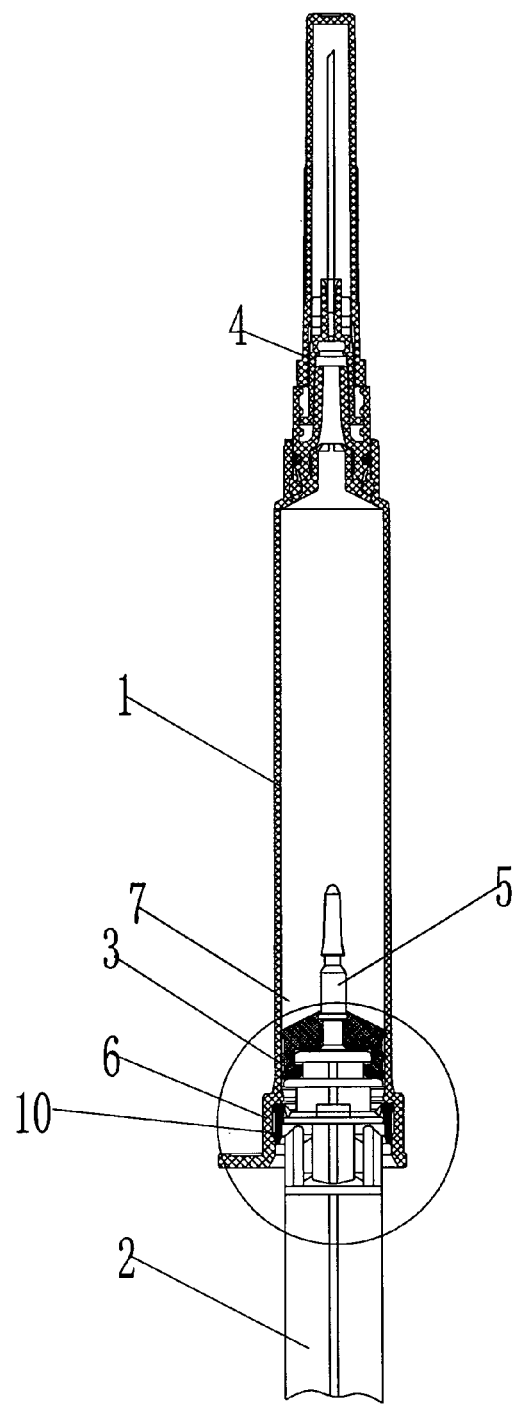
FIG. 2 is a sectional view of the syringe during the push rod is installed.

As shown in FIG. 1 and FIG. 2, the present invention includes a hollow barrel 1, a push rod 2 sliding within the barrel 1, a rubber plug 3 in front of the push rod 2, and a needle seat 4 in front of the barrel 1; in this embodiment, a clamping core 5, located at the front end of the push rod 2, can be integrated with the push rod 2 through injection moulding; certainly, other push rod can also be adopted so long as it is structurally suitable to the syringe.

Figure 9:
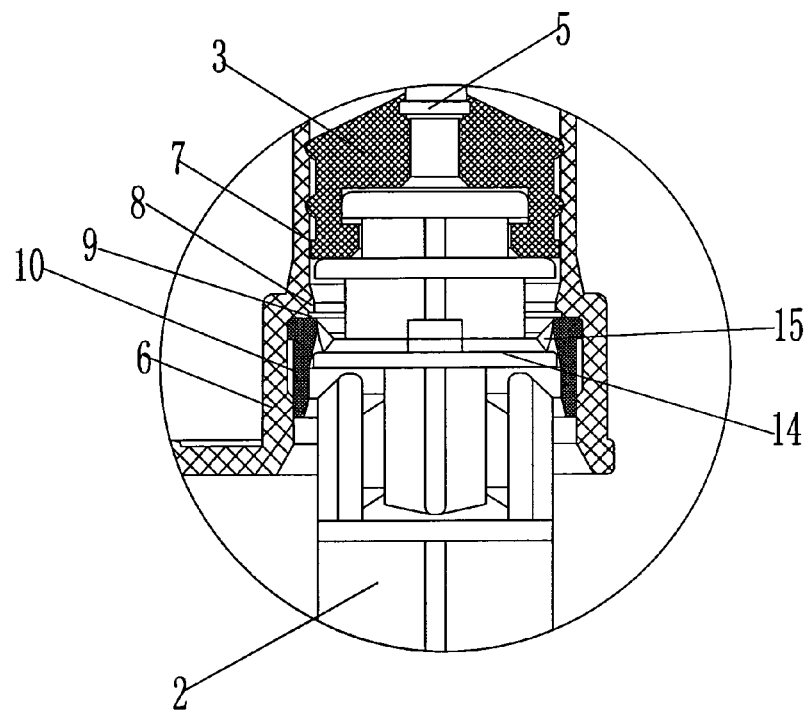
FIG. 9 is a partial enlarged view of FIG. 1.

As shown in FIG. 9, the present invention is improved in the following aspects: The push rod 2 is provided with a round platform 14, which is provided with an elastic ratchet 15 that slantingly extends toward the inner wall of the barrel; the barrel is provided at the end with an increasing-diameter portion 6; at the transient position between the normal-diameter portion 7 and the increasing-diameter portion 6 of the barrel is located a slanting step 8, below which is a groove 9 where the elastic ratchet 15 can be catched when the push rod is drawn backward; and the increasing-diameter portion 6 is provided inside with a circlip 10 that can press against the bottom of the round platform 14.

Figure 12:
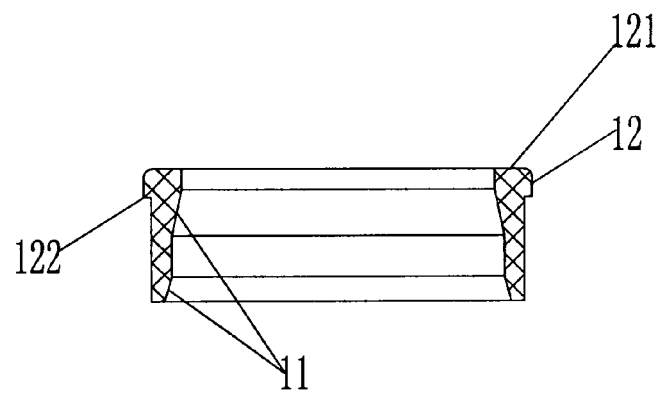
FIG. 12 is a sectional view of the circlip.

As shown in FIG. 10, FIG. 11 and FIG. 15, the push rod 2 is provided below the rubber plug 3 with a round platform 14, whose external diameter is smaller than or equal to the minimal internal diameter of the barrel at the slanting step 8, but bigger than the minimal internal diameter of the circlip 10; the round platform 14 is provided with an elastic ratchet 15 that slantingly extends toward the inner wall of the barrel; there are at least two elastic ratchets 15 that are symmetrically positioned; there are preferably four elastic ratchets 15 that are symmetrically positioned; the distance between the symmetrical ratchet tips is smaller than the internal diameter of the normal-diameter portion 7 of the barrel, but bigger than the minimal internal diameter of the barrel at the slanting step 8; and the tip of the elastic ratchet 15 extends slantingly up to the front end of the barrel. As shown in FIG. 14, the groove 9 is a circle of clamping groove along the circumference, whose upper end plane 91 is a slope or a plane that extends outward along the direction of the tip of the elastic ratchet 15; and the diameter of the groove at the side wall 92 is bigger than the distance between the tips of the symmetrically-positioned elastic ratchets 15. As shown in FIG. 11 and FIG. 12, the circlip 10, dynamically fitted with the inner wall of the increasing-diameter portion 6 at the end of the barrel, can move forward and backward axially without moving out of the barrel, with the moving distance longer than the distance from the tip of the elastic ratchet 15 on the push rod 2 to the bottom of the round platform 14; the upper end of the circlip 10, whose internal diameter is slightly smaller than that of the barrel at the slanting step 8, can press against the bottom of the round platform 14. The circlip 10 is provided at the inner circle with a slope 11; when the push rod is installed, the elastic ratchet 15 can move forward and furl inward along the slope, and the round platform 14 can stretch the inner bore of the circlip 10 larger and get into it. The increasing-diameter portion 6 at the end of the barrel is provided on the inner wall with a circle of big groove 61 that is dynamically fitted with the circlip 10; the big groove 61 can butt at its upper end 62 against the top end 121 of the circlip 10, and is provided at the lower end with a flanged step 13; the circlip 10 is provided at the upper outer circle with a flange 12; the flanged step 13 butts against the bottom end plane 122 of the flange 12; and the step 13 prevents the circlip 10 from sliding out of the barrel. As shown in FIG. 13, when the push rod 2 is drawn backward to the bottom of the barrel after injection, the bottom plane of the round platform 14 on the push rod 2 will get in touch with the top plane of the circlip 10 installed within the barrel 1; since the internal diameter of the circlip 10 is smaller than the external diameter of the round platform 14, the circlip 10 is brought to move backward; when the push rod 2 is drawn further backward, the elastic ratchet 15 will get in touch with the upper slope 81 of the slanting step 8, experience elastic deformation toward the center of the push rod under the action of this slope 81, and move across the minimal-inner-diameter point of the slanting step 8 along with the backward movement of the push rod; the elastic ratchet 15, after moving across the point, restores its natural state by its own elasticity, and its tip will get stuck into the groove 9 below the slanting step 8; when the push rod 2 continues to move backward, the bottom end plane 122 of the flange 12 at the upper end of the circlip 10 will butt against the flanged step 13 on the inner wall of the increasing-diameter portion 6 at the end of the barrel, which may prevent the push rod from moving backward; if a certain force is applied to push the push rod forward in the injecting direction, the elastic ratchet 15 will prevent the movement under the action of the groove 9; the side wall 92 of the groove 9 can prevent the elastic ratchet from overturning along the wall of the barrel; and thus the push rod is locked. In order to make the self-destroying process more complete, the push rod 2 can further be provided with some defective points; in this embodiment, four defective points A, B, C and D are provided; when being drawn backward after injection, the push rod 2 may be pulled apart at the defective points; since the push rod 2 has been locked this time, it cannot be reused or replaced, thus ensuring complete self-destroying of the syringe.

Figure 3:
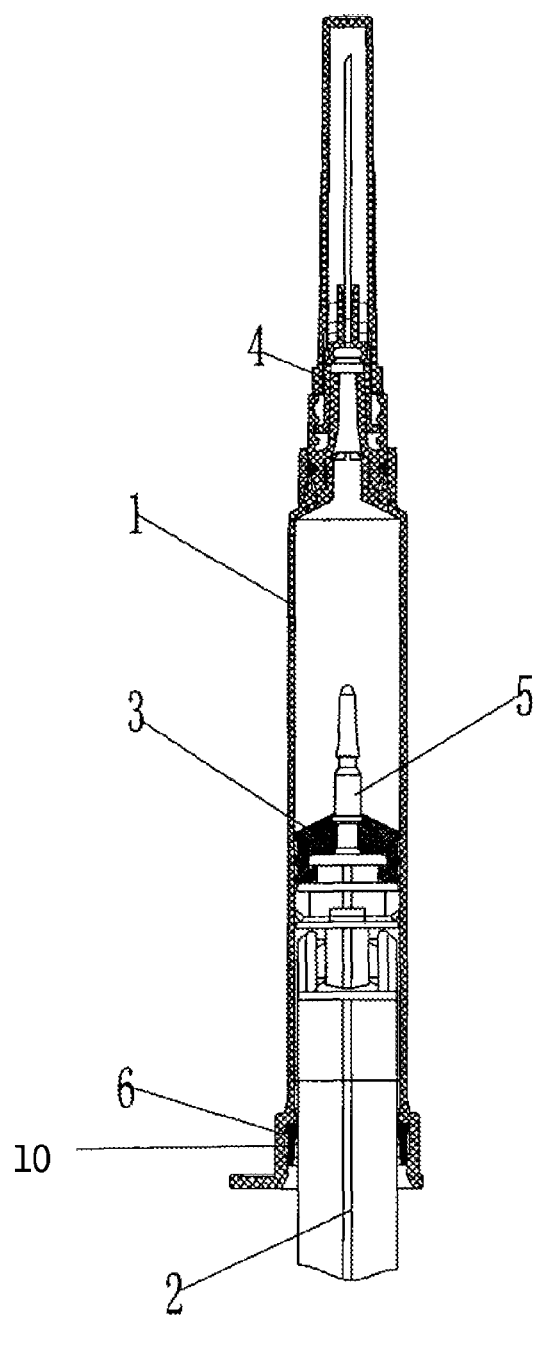
FIG. 3 is a sectional view of the syringe after the push rod is installed.
Figure 4:
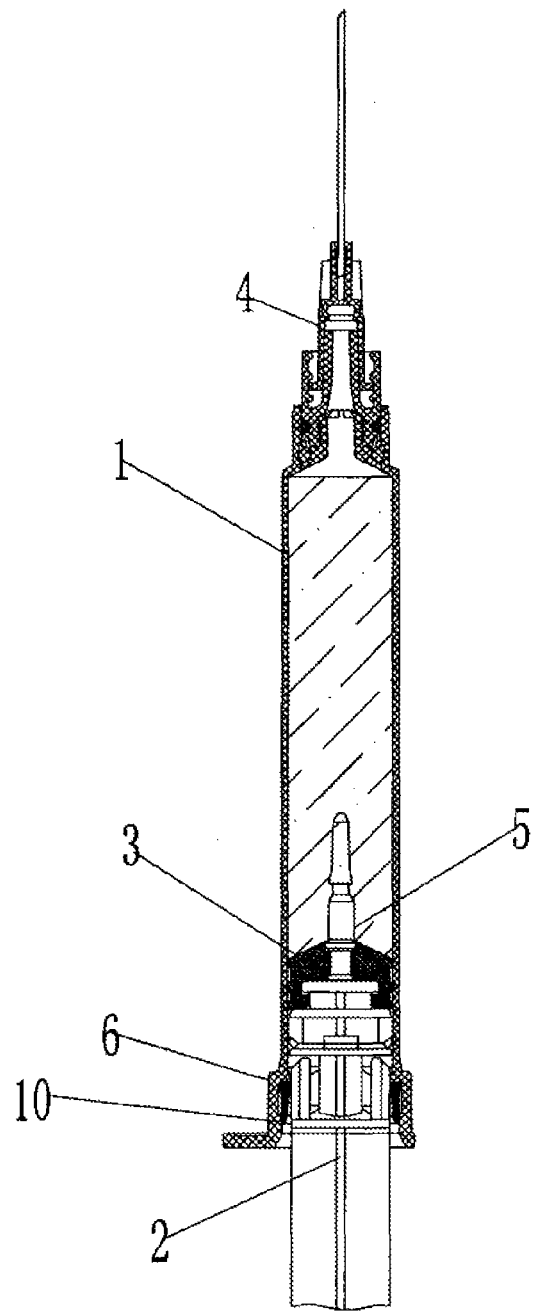
FIG. 4 is a sectional view of the syringe that has taken in the fluid.
Figures 7, 8:
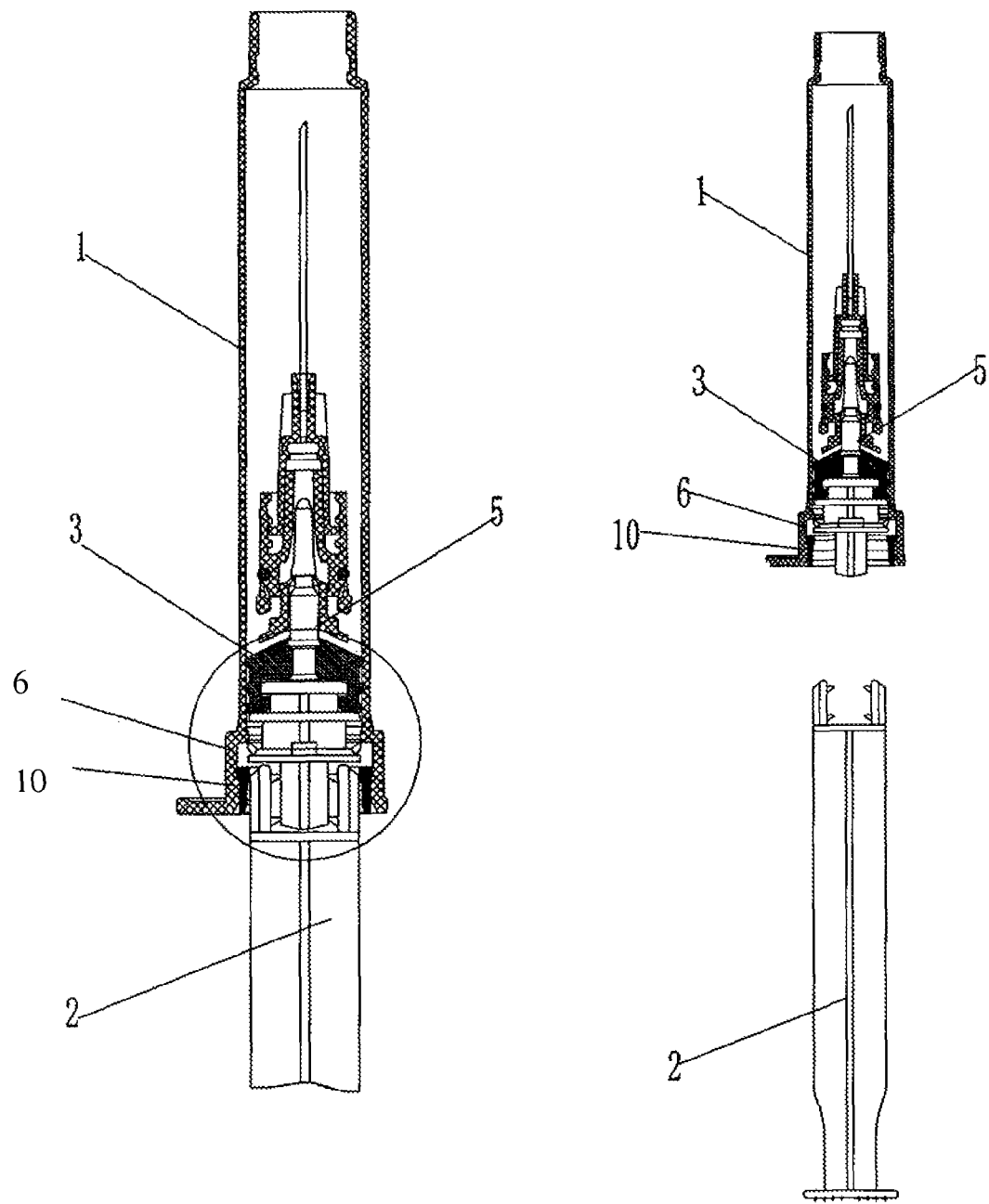
FIG. 7 is a sectional view of the syringe after the self-destroying process.
FIG. 8 is a sectional view of the syringe with its push rod broken.

During application of the present invention: First, as shown in FIG. 1 where the syringe has not been assembled together, the push rod 2 has not been pushed into the barrel yet, and the circlip 10 is limited at the end of the barrel by the flange 12 on the inner wall of the barrel. Then, as shown in FIG. 2 where the push rod 2 has been installed in the barrel, the elastic ratchet 15 on the push rod 2 moves forward along the slope 11 of the circlip 10, and meanwhile the circlip 10 along the inner wall of the barrel from the point 61 to the point 62; and the elastic ratchet 15 furls inward under the pressure of the circlip 10. As shown in FIG. 3, since the upper end of the circlip 10, whose internal diameter is smaller than that of the barrel at the slanting step 8, the elastic ratchet 15, under the action of the circlip 10, can smoothly move through the slanting step 8 into the normal-diameter portion of the barrel; and the round platform 14, through stretching the inner bore of the circlip 10 larger, can get into the normal-diameter portion of the barrel as well. FIG. 4 shows the syringe that has taken in the fluid. FIG. 5 shows the syringe that has finished injection. As shown in FIG. 6, the needle seat 4 is apart from the barrel, which is the first step of the self-destroying process; this time the push rod is pulled backward, which will bring the needle seat 4 to retract, and meanwhile the elastic ratchet 15 will slide backward along the slanting step 8, as shown in FIG. 7 and FIG. 13; this time the elastic ratchet 15 gets stuck into the groove 9 located below the slanting step 8, and the push rod 2 is locked, thus completing the self-destroying process. As shown in FIG. 8, the push rod 2 is pulled apart at the defective points, and thus completely destroyed.

In the above technical solution, the syringe in the embodiment adopts the retractable needle. However, the improved technical solution described in the present invention is not limited to this type of syringe, but applicable to other types of syringes with nonretractable needles as well. Since various variations and modifications may be made without departing from the spirit and scope of the invention, all equivalent technical solutions are included in the present invention.

The invention claimed is:

1. A new self-locking self-destroying safety syringe, specifically for use in medical treatment, comprising,
    a hollow barrel;
    a push rod sliding within the barrel;
    a rubber plug in front of the push rod;
    a needle seat in front of the barrel;
    the push rod is drawn backward to make the needle seat retract and be apart from the barrel after injection;
    the push rod is provided with a round platform, which is provided with at least one elastic ratchet that slantingly extends toward an inner wall of the barrel;
    the barrel is provided at a back end with an increasing-diameter portion;
    at a transient position between a normal-diameter portion and the increasing-diameter portion of the barrel is located a slanting step, and a groove is formed below and adjacent to the slanting step;
    when the push rod is drawn backward, the elastic ratchet passes by the slanting step and is caught in the groove;
    the increasing-diameter portion of the barrel is provided inside with a circlip;
    an external diameter of the round platform on the push rod is smaller than or equal to a minimal internal diameter of the barrel at the slanting step, but bigger than a minimal internal diameter of the circlip; and
    when the push rod is drawn backward, the circlip presses against the side of the round platform facing the push rod.

2. The new self-locking self-destroying safety syringe according to claim 1, being characterized in that the circlip, dynamically fitted with an inner wall of the increasing-diameter portion at the end of the barrel, can move forward and backward axially without moving out of the barrel, with the moving distance longer than the distance from the tip of the elastic ratchet on the push rod to the bottom of the round platform; the internal diameter of the upper end of the circlip is slightly smaller than that of the barrel at the slanting step; the circlip is provided at an inner circle with a slope; when the push rod is installed, the elastic ratchet can move forward and furl inward along the slope, and the round platform can stretch an inner bore of the circlip larger to get into it.

3. The new self-locking self-destroying safety syringe according to claim 2, being characterized in that there are at least two elastic ratchets that are symmetrically positioned; the distance between the symmetrical ratchet tips is smaller than the internal diameter of the normal-diameter portion of the barrel, but bigger than the minimal internal diameter of the barrel at the slanting step.

4. The new self-locking self-destroying safety syringe according to claim 2, being characterized in that the tip of the elastic ratchet extends slantingly up to the front end of the barrel.

5. The new self-locking self-destroying safety syringe according to claim 2, being characterized in that there are four elastic ratchets that are symmetrically positioned.

6. The new self-locking self-destroying safety syringe according to claim 1, being characterized in that the increasing-diameter portion at the end of the barrel is provided on the inner wall of the barrel with a circle of big groove that is dynamically fitted with the circlip; the big groove can butt at its upper end against a top end of the circlip, and is provided at the lower end with a flanged step; the circlip is provided at an upper outer circle with a flange; and the flanged step butts against an bottom end plane of the flange.

7. The new self-locking self-destroying safety syringe according to claim 1, being characterized in that there are at least two elastic ratchets that are symmetrically positioned; the distance between the symmetrical ratchet tips is smaller than the internal diameter of the normal-diameter portion of the barrel, but bigger than the minimal internal diameter of the barrel at the slanting step.

8. The new self-locking self-destroying safety syringe according to claim 1, being characterized in that the tip of the elastic ratchet extends slantingly up to the front end of the barrel.

9. The new self-locking self-destroying safety syringe according to claim 1, being characterized in that there are four elastic ratchets that are symmetrically positioned.

* * * * *